United States Patent [19]

Tanaka et al.

[11] 4,339,318

[45] Jul. 13, 1982

[54] OXYGEN GAS ANALYZING DEVICE

[75] Inventors: Takeo Tanaka; Osamu Yamamoto, both of Kawasaki, Japan

[73] Assignee: Fuji Electric Co., Ltd., Kanagawa, Japan

[21] Appl. No.: 218,237

[22] Filed: Dec. 19, 1980

[30] Foreign Application Priority Data

Dec. 27, 1979 [JP] Japan ............................ 54/180331[U]
Nov. 4, 1980 [JP] Japan ............................ 55/157769[U]

[51] Int. Cl.³ .............................................. G01N 27/58
[52] U.S. Cl. .................................................. 204/195 S
[58] Field of Search ............................. 204/1 S, 195 S

[56] References Cited

U.S. PATENT DOCUMENTS 3,859,192  1/1975  Barnes et al. ................... 204/195 S
4,251,342  2/1981  Habdas et al. ................. 204/195 S Primary Examiner—G. L. Kaplan
Attorney, Agent, or Firm—Sughrue, Mion, Zinn, Macpeak & Seas

[57] ABSTRACT

An oxygen gas analyzing device in which gas sampled from a flue is analyzed without the need of an external driving source. A sampling tube protrudes into a flue through a wall thereof. A partition board divides the gas sampling tube extending from the protruding end of the tube forming gas flow-in and flow-out paths. A solid electrolytic element is positioned in a ceramic tube having one end open to the outer end of the gas sampling tube. A heater is provided in the walls of the ceramic tube.

11 Claims, 17 Drawing Figures

FIG. 3
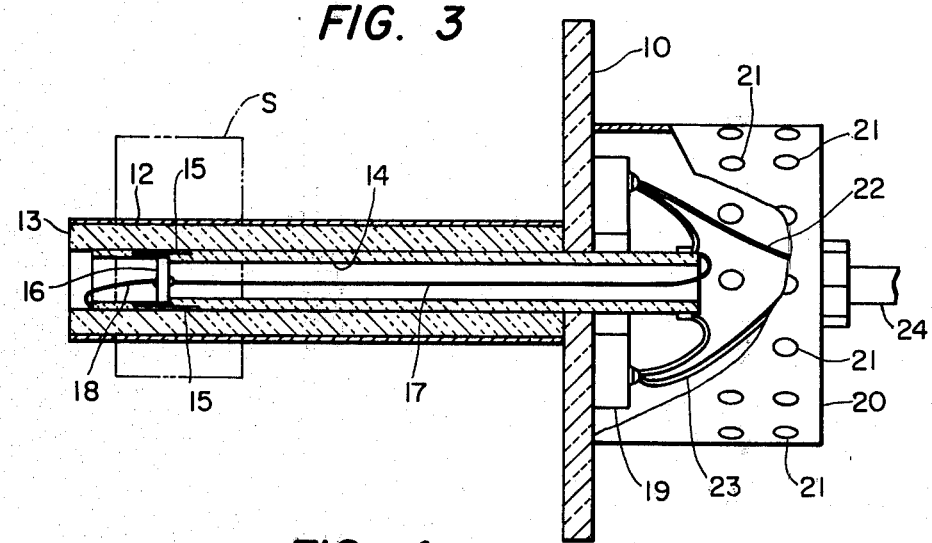
FIG. 4
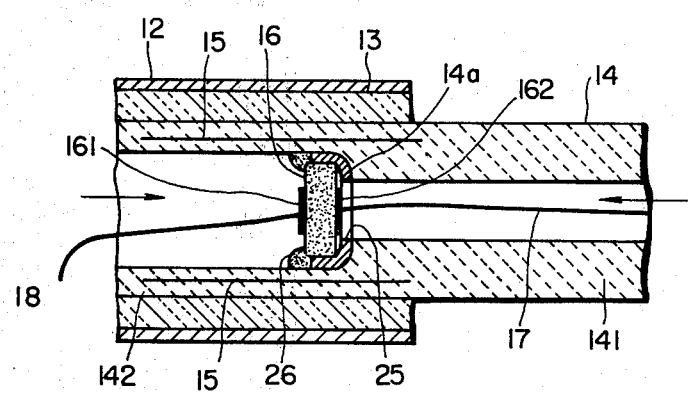
FIG. 5A  FIG. 5B  FIG. 6A  FIG. 6B
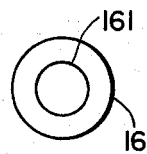 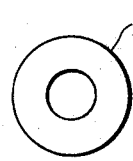 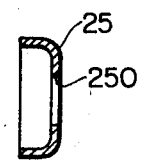

OXYGEN GAS ANALYZING DEVICE

BACKGROUND OF THE INVENTION

The present invention relates to an oxygen gas analyzing device for measuring the oxygen content, or density, of gas in a flue.

Heretofore, gas in a flue was sampled with a gas sampling tube in an oxygen gas analyzing device of the general type to which the invention pertains. The gas is sampled by extracting a sample with a gas suction device such as a pump or an ejector and the gas thus sampled is supplied to the analyzing device which is positioned externally. After analyzation, the sample is discharged into the atmosphere. This system suffers from difficulties in that the tubing of the device can be corroded or clogged since the temperature of the gas which was high in the flue is decreased to room temperature and in that it is necessary to provide a driving source for gas suction.

An object of the invention is thus to provide an oxygen content measuring device which is free of the above-described problems accompanying a prior art device of this type. More specifically, an object of the invention is to provide a solid electrolytic element type oxygen gas analyzing device based on a direct coupling system in which no drains are required for a sampled gas and the provision of a driving source is unnecessary for sampling the gas.

SUMMARY OF THE INVENTION

These and other objects of the invention are met by a solid electrolytic element type oxygen gas analyzing device for analyzing the oxygen content of a gas which is sampled with a gas sampling tube protruding into a flue through a wall of the flue. A partition board is provided in the gas sampling tube extending from the end of the gas sampling tube protruding into the flue inwardly of the gas sampling tube and dividing the interior of the gas sampling tube into a gas flow-in path and a gas flow-out path so that the dynamic pressure of the gas flowing in the flue causes the gas to enter the gas sampling tube through the gas flow-in path to contact the oxygen gas analyzing element, turn at the end of the partition board and flow through the gas flow-out path to return to the flue.

The foregoing object and other objects of the invention have also been achieved by the provision of an oxygen gas analyzing device in which a solid electrolytic element is joined to a ceramic tube by an adhesive in such a manner that, at the open ends of the solid electrolytic element and the ceramic tube, the adhesive covers the inner wall and the end face of the solid electrolytic element, extends into the gap between the solid electrolytic element and the magnetic tube and covers the end face and the outer wall of the magnetic tube.

BRIEF DESCRIPTION OF THE DRAWINGS

FIG. 3 is a sectional view showing the arrangement of a preferred embodiment of a solid electrolytic element type oxygen gas analyzing device;

FIG. 4 is an enlarged sectional view showing portions of the device of FIG. 3;

FIG. 5A is a plan view and

FIG. 5B a longitudinal sectional view of the solid electrolytic element of FIG. 4;

FIG. 6A is a plan view and

FIG. 6B is a sectional view showing a metal packing of the device of FIG. 4;

DESCRIPTION OF THE PREFERRED EMBODIMENTS

Preferred embodiments of the invention will be described in detail with reference to the accompanying drawings.

Figure 1:
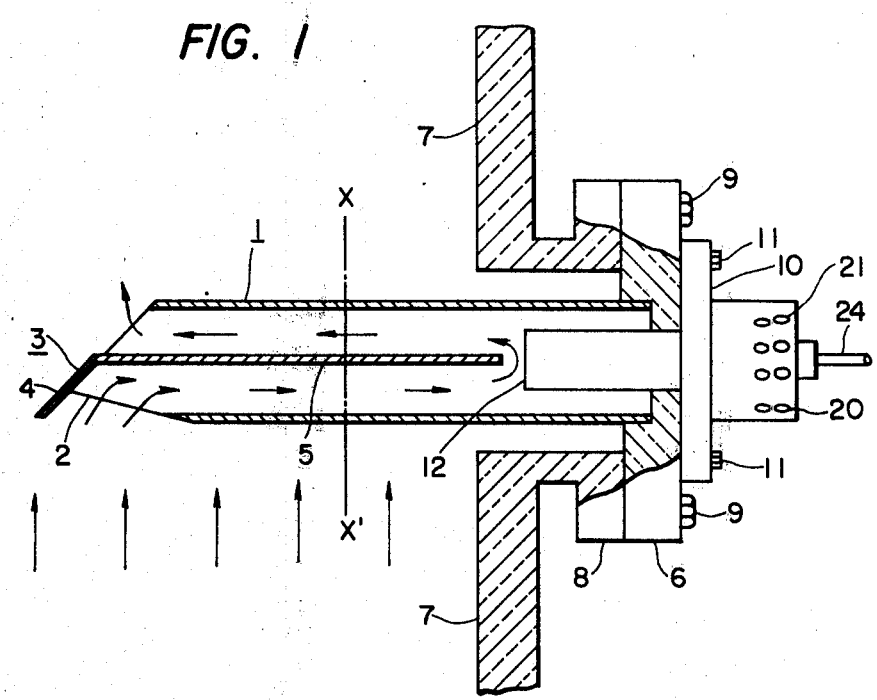
FIG. 1 is a sectional side view showing a first embodiment of an oxygen content measuring device of the invention.
Figure 2A:
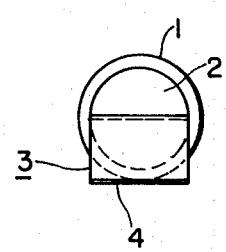
FIG. 2A is a front view of a gas sampling tube of the device of FIG. 1.

FIG. 1 is a sectional side view showing a first embodiment of the invention. FIG. 2A is a front view of a gas sampling tube of the device shown in FIG. 1, FIG. 2B a sectional view taken along line X—X' in FIG. 1, and FIG. 2C a perspective view showing an end portion of the sampling tube from which the partition board has been removed.

Referring FIG. 1, a flange 6 is mounted on the flange 8 of a flue 7 with bolts 9. The base of a gas sampling tube 1 is welded to the flange 6 with the end portion of the gas sampling tube 1 extending into the flue 7. A flange 10 is fixedly secured to the flange 6 with bolts 11. A protective sleeve 12 in which a solid electrolytic element type oxygen gas analyzing device is placed is secured to the central portion of the flange 10. The protective sleeve 12 is inserted through the central hole of the flange 6 into the gas sampling tube 1. In FIG. 1, reference numeral 20 designates a cover for the air contact side of the oxygen gas analyzing device located in the protective sleeve 12, the cover 20 having a number of small holes 21 through which the air flows, and reference numeral 24 designates a cable for carrying an analyzation output.

Figure 2B:
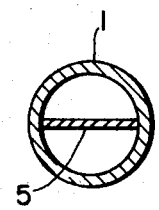
FIG. 2B is a sectional view of the gas sampling tube taken along line X—X in FIG. 1.
Figure 2C:
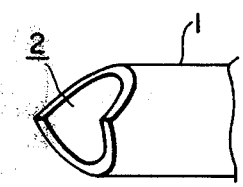
FIG. 2C is a perspective view of the end portion of the gas sampling tube of FIG. 1 from which a partition board has been removed.

The gas sampling tube 1 is made of stainless steel, for instance, and its end portion is cut obliquely from both sides as shown in FIG. 2C while its base is fixedly welded to the flange 6 as described above. The tube 1 has a partition board 3 including a flat portion 5 and a bent portion 4. More specifically, as shown in FIG. 1, FIGS. 2A and 2B, the flat portion 5 of the partition board 3 is inserted into the gas sampling tube 1 with the bent portion 4 extending outwardly and down. The gas flowing in the flue is caught by the bent portion 4, introduced along one side of the flat portion 5 of the partition board into the gas sampling tube 1, brought into contact with the electrodes of the gas analyzing device located in the protective sleeve 12, and runs along the other side of the flat portion 5 to return to the flue as indicated by the arrows. The gas from the flue is allowed to flow along the above-described path by its own dynamic pressure. The end portion of the gas sampling tube 1 protrudes to the central axis of the flue. With this structure, even if eddy currents of gas are present along the wall of the flue, the flow of gas in the gas sampling tube is not affected.

FIG. 3 is a sectional view showing the construction of the solid electrolytic element type oxygen gas analyzing device positioned in the protective sleeve 12 shown in FIG. 1.

As shown in FIG. 3, the gas analyzing device includes a ceramic tube 14 made of alumina or the like which is adapted to hold a solid electrolytic element 16 which may be a so-called "zirconia element". The ceramic tube 14 is covered with a thermal insulator 13. These components are placed in the protective sleeve 12. One end of the protective sleeve 12 is welded to one side of the flange 10 and a terminal stand 19 and the cover 20 are mounted on the other side of the flange 10. The cover 20 has a number of small holes 21 for introducing a medium having a known or standard oxygen content (air in this embodiment) into the ceramic tube 14. A heater element 15 buried in the wall of the ceramic tube 14 is provided for heating the solid electrolytic element 16. Electric power is supplied through wires 23 to the heater element 15. The heater element 15 is formed in a zigzag state in the wall of the ceramic tube 14. Leads 17 and 18 are connected between the electrodes (not shown in FIG. 3) and the signal lines 22. The signal lines 22 and the wires 23 from the aforementioned cable 24 which extends to the outside and is there connected to an indicator (not shown).

FIG. 4 is an enlarged sectional view showing portions S of the analyzing device of FIG. 3. FIGS. 5A and 5B are a plan view and a longitudinal sectional view, respectively, of the solid electrolytic element 16 of FIG. 4. FIGS. 6A and 6B are a plan view and a sectional view, respectively, showing a metal packing in the device as shown in FIG. 4.

Referring to FIG. 4, the ceramic tube 14 is formed as a cylindrical tube of alumina the outside diameter of which is uniform throughout its length. However, the ceramic tube 14 has two different inside diameters, namely, a small inside diameter and a large inside diameter. That is, the ceramic tube 14 is made up of a small inside diameter portion 141 and a large inside diameter portion 142. An annular mounting seat 14a is formed at the boundary between the small inside diameter portion 141 and the large inside diameter portion 142. The heater element 15 is circumferentially buried in the wall of the ceramic tube 14 so that it covers at least the region of the mounting seat 14a. The insulator 13 is provided around the ceramic tube 14 covering the region of the heater element 15. The wires connected to the heater element 15 extend from the end face of the small inside diameter portion of the ceramic tube 14.

A disc-shaped zirconia element forming the solid electrolytic element 16 is held in place by the metal packing 25 on the mounting seat 14a of the ceramic tube 14. Since the metal packing 25 is heated to about 850° C. by the heater element 15 during measurements, it is necessary that the metal packing 25 be made of a material which is stable at high temperature. The packing 25 is so shaped as to cover the mounting seat 14a and parts of the cylindrical wall of the zirconia element 16. The assembly of the packing 25 and the zirconia element 16 are heated to about 600° C. to 800° C. and the zirconia element is then pressed into the mounting seat 14a. Thus, the ceramic tube 14, the packing 25 and the zirconia element 16 are combined rigidly in a single unit. In order to thermally press fit the packing 25 and the zirconia element 16 into the mounting seat 14a, it is necessary that the material of the packing 25 be a metal which is stable and soft at high temperatures. The most suitable metals which can satisfy this requirement are platinum and gold. In order to positively prevent the zirconia element 16 and the packing 25 from dislodging from the ceramic tube 14, the zirconia element 16 and the packing 25 are bonded to the ceramic tube 14 with a ceramic adhesive 26. Porous electrodes 161 and 162 are secured to both sides of the zirconia element 16 and are connected to the leads 17 and 18 which extend beyond the ceramic tube 14. The structure of the electrodes 161 and 162 secured to the zirconia element 16 is as shown in FIG. 5B.

In the oxygen gas analyzing device thus constructed, the reference oxygen medium (air) is introduced into the small inside diameter portion 141 of the ceramic tube 14, contacting the electrode 162 of the zirconia element 16, while the gas to be measured is introduced into the large inside diameter portion 142 of the ceramic tube 14, contacting the electrode 161 of the zirconia element 16. As a result, an electromotive force is induced in the zirconia element 16 according to the well-known Nernst equation. From the measured electromotive force and with the use of this equation, the oxygen content in the gas under test can be determined. The electromotive force or voltage is transmitted to the outside through the electrodes 161 and 162 and the leads 17 and 18.

The Nernst equation is as follows:

$$E = 55.7 \log (P_C/P_A).$$

In this equation, $P_C$ is the partial pressure of oxygen in a gas (or a solid) whose oxygen density is known, for instance the partial pressure of oxygen in the air, and $P_A$ is the partial pressure of oxygen in the gas to be measured. Accordingly, the oxygen content of the gas to be measured can be determined by measuring the electromotive force E.

Figure 7:
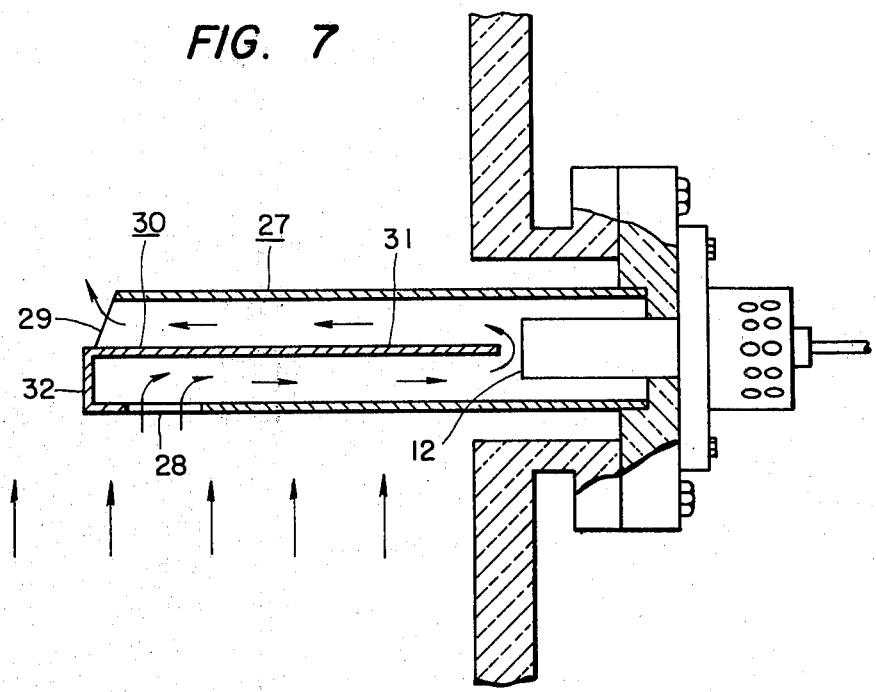
FIG. 7 is a sectional side view showing another embodiment of the invention.

FIG. 7 is a longitudinal sectional view showing another embodiment of the invention.

The embodiment shown in FIG. 7 differs from that shown in FIG. 1 only in the construction of the gas sampling tube 27. Specifically, the end portion of the gas sampling tube 27 is modified by forming an opening 29 in a part of the end of the gas sampling tube 27 with the remainder of this part being closed by the bent portion 32 of the partition board 30 and with a hole 28 cut in the other part of the end portion of the wall of the gas sampling tube 27. Accordingly, the gas flowing in the flue, as indicated by the arrows in FIG. 7, enters the sampling tube 27 through the hole 28 by its own dynamic pressure, advances along one side of the flat portion 31 of the partition board 30 contacting the electrode in the protective sleeve 12, and advances along the other side of the flat portion 31 to return to the flue through the opening 29.

Figure 8:
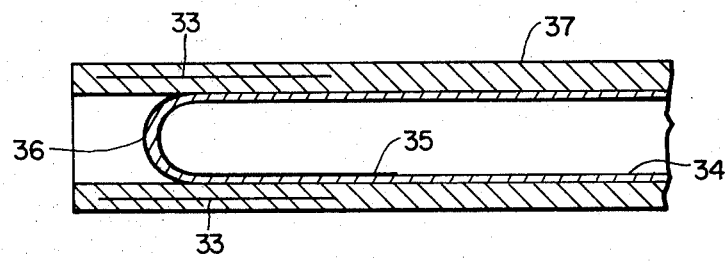
FIG. 8 is a sectional side view showing a modification of a zirconia element employed in the invention.

FIG. 8 is a sectional side view of a modification of the zirconia element (i.e., the solid electrolytic element) employed in the invention. As shown in FIG. 8, a zirconia element 34 having the shape of a test tube is inserted into a ceramic tube 37. In FIG. 8, reference numeral 33 designates a heater element, and 35 and 36 electrodes. With the zirconia element shaped as shown in FIG. 8 employed in place of the disc-shaped zirconia element of FIG. 4, the same effects are obtained.

Figure 9:
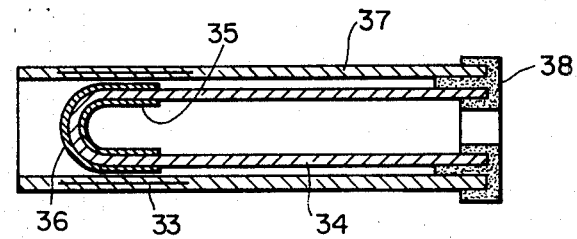
FIG. 9 is a longitudinal sectional view of the embodiment of FIG. 8.
Figure 10:
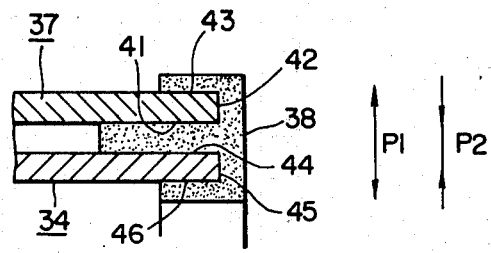
FIG. 10 is an enlarged view showing parts of the embodiment of FIG. 8.

As shown in FIG. 9, the solid electrolytic element 34 of the FIG. 8 embodiment is coupled to the ceramic tube 37 with a inorganic adhesive 38 which is applied to the open ends of the solid electrolytic element 34 and the ceramic tube 37 which are substantially flush with each other. More specifically, as shown in FIG. 10 which is an enlarged view of a part of the end portion of the assembly shown in FIG. 9, the non-organic adhesive 38 is applied to the open ends of the solid electrolytic element 34 and the ceramic tube 37 in such a manner that it covers a part of the inner wall 46 of the solid electrolytic element 34 and the end face 45 thereof, extends into the gap between the outer wall 44 of the solid electrolytic element and the inner wall 41 of the ceramic tube 37, and covers the end face 42 of the ceramic tube 37 and a part of the outer wall 43 thereof. Examples of suitable non-organic adhesives are alumina adhesive, silica adhesive, zirconia adhesive, and magnesia adhesive.

With the solid electrolytic element 34 secured to the ceramic tube 37 by the adhesive as described with reference to FIGS. 9 and 10, if stress is imposed on the oxygen analyzing device tending to pull the solid electrolytic element 34 and the ceramic tube 37 away from each other in the directions of the arrow $P_1$, the adhesive 38 may peel off the surface 41 and 44 but the adhesive 38 is maintained satisfactorily in close contact with the surfaces 43 and 46. That is, the solid electrolytic element 34 and the ceramic tube 37 are maintained coupled to each other and sealed hermetically. If stress acting on the device urges the electrolytic element 34 and the ceramic tube 37 closer to each other in the directions of the arrow $P_2$, the stress tends to compress the surfaces 41 and 44. Accordingly, in this case also, the coupling condition and hermetically sealing condition of the solid electrolytic element 34 and the ceramic tube 37 are satisfactorily maintained.

Since the non-organic adhesive 38 is relatively porous, it may be difficult to completely hermetically seal the gap between the solid electrolytic element 34 and the ceramic tube 37 with a non-organic adhesive. Therefore, a gas to be measured or the oxygen reference medium may pass through a non-organic adhesive. Such incomplete gas-tightness is preferably prevented because it will decrease the measurement accuracy.

In general, the pressure of the gas to be measured is higher than that of the oxygen reference medium. Therefore, it is necessary to prevent the passage of the gas to be measured rather than the passage of the oxygen reference medium. This problem is solved in the embodiment of the oxygen analyzing device of the invention shown in FIGS. 11 and 12 in which the passage of gas through the joint of the solid electrolytic element and the ceramic tube is prevented.

Figure 11:
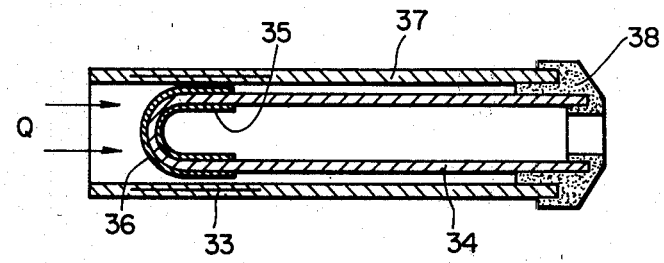
FIG. 11 is a longitudinal sectional view of another embodiment of an oxygen analyzing device according to the invention.
Figure 12:
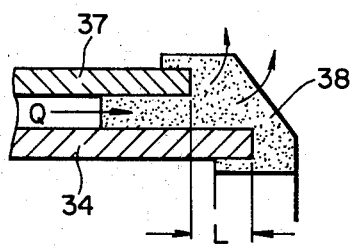
FIG. 12 is an enlarged view showing components of the oxygen analyzing device in FIG. 11.

The fundamental construction of the oxygen analyzing device shown in FIGS. 11 and 12 is similar to that of the device shown in FIGS. 9 and 10 except that at the joint the open end of the solid electrolytic element 34 protrudes by a length L from the open end of the ceramic tube 37. In this embodiment, the joint made by the adhesive functions to connect the solid electrolytic element 34 and the ceramic tube 37, as before. In addition to this, even in the case where the gas to be measured introduced into the gap between the solid electrolytic element 34 and the ceramic tube 37 from the other end of the ceramic tube 37 as indicated by the arrow Q has passed through the adhesive 38 or the joint, the gas can be discharged to the outside without it reaching the interior of the solid electrolytic element 34. In practice, a distance L of no more than several millimeters, suffices for this effect, and therefore the protrusion of the solid electrolytic element will not disturb the connection of the solid electrolytic element and the ceramic tube. Thus, mixing of a gas to be measured with the oxygen reference medium is prevented and accordingly the measurement accuracy is maintained.

Figure 13:
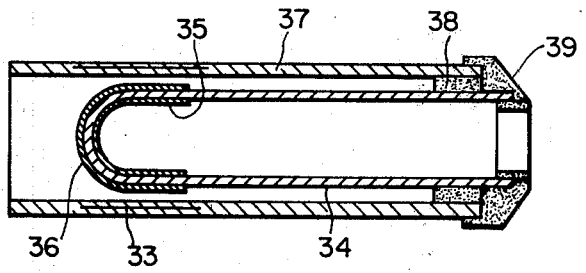
FIG. 13 is a longitudinal sectional view of yet another embodiment of an oxygen analyzing device according to the invention.

Organic adhesives are generally superior to non-organic adhesives in gas tightness while the converse is true for bonding strength. The advantages of both types of adhesive are effectively utilized in the embodiment of oxygen analyzing device of the invention shown in FIG. 13. In the embodiment of FIG. 13, the joint is formed by non-organic adhesive 38 in the gap between the solid electrolytic element 34 and the ceramic tube 37 and organic adhesive 39 applied to the remaining portions. The organic adhesive 39 may be, for instance, an epoxy adhesive or a silicone adhesive.

As is apparent from the above description, according to the solid electrolytic element type oxygen gas analyzing device of the invention, the provision of a driving source is unnecessary to sample a gas to be measured which is flowing in a flue. Accordingly, the oxygen gas analyzing device of the invention is advantageous in that it is simple in construction and the manufacturing cost thereof is low while its reliability is high. Furthermore, because the gas is brought directly into contact with the solid electrolytic element, no components having temperature gradients are necessary as a result of which no drain is created in the system. Thus, the oxygen gas analyzing device of the invention is meritorious in that its maintenance is simple.

With the device of the invention, if a thermal stress or a mechanical stress acts on the solid electrolytic element and the ceramic tube or the adhesive, the adhesive will not come off the solid electrolytic element and the ceramic tube. That is, the solid electrolytic element and the ceramic tube are maintained satisfactorily hermetically sealed.

What is claimed is:

1. An oxygen gas analyzing device comprising: a solid electrolytic element having an oxygen ion dependent conductivity; first and second porous electrodes provided on respective first and second sides of said element; a gas sampling tube adapted to protrude into a flue through a wall of said flue, said sampling tube bringing gas from said flue into contact with said first electrode while an oxygen reference medium is brought into contact with said second electrode to generate an electromotive force between said two electrodes corresponding to the oxygen density of said gas; a hollow cylindrical ceramic tube; said solid electrolytic element being disposed in said cylindrical ceramic tube, dividing the hollow interior of said ceramic tube into first and second interior portions; a heater element for heating said solid electrolytic element disposed in the wall of said ceramic tube, said oxygen reference medium being introduced through one end of said ceramic tube to contact said second electrode while said gas from said flue is introduced through said gas sampling tube and through the other end of said ceramic tube to contact said first electrode; and a partition board provided in said gas sampling tube extending toward said ceramic tube from a protruding end of said gas sampling tube in said flue to divide the interior of said gas sampling tube into a gas flow-in path and a gas flow-out path, wherein the dynamic pressure of said gas flowing in said flue causes said gas to enter said gas sampling tube through said gas flow-in path to contact said first electrode, turn at the end of said partition board and flow through said gas flow-out path to return to said flue.

2. The oxygen gas analyzing device as claimed in claim 1 further comprising a protective sleeve disposed around said ceramic tube.

3. The oxygen gas analyzing device as claimed in claim 2 further comprising a cover having holes therein covering the end of said ceramic tube through which said oxygen reference medium is introduced.

4. The oxygen gas analyzing device as claimed in claim 1 wherein said first and second interior portions are of different diameters and wherein said element is disc shaped and positioned at the juncture of said first and second interior portions with its center axis aligned substantially with the longitudinal axis of said ceramic tube.

5. The oxygen gas analyzing device as claimed in claim 4 further comprising a metal packing for mounting said element at said juncture between said first and second interior portions, said metal packing being cup-shaped with an open bottom.

6. The oxygen gas analyzing device as claimed in claim 1 wherein said element has the shape of a test tube having a curved bottom portion directed toward said flue.

7. The oxygen gas analyzing device as claimed in claim 6 wherein said element is joined to said ceramic tube by an adhesive wherein, at open ends of said element and said ceramic tube, said adhesive covers the inner wall and end face of said element, extends into a gap between said element and said ceramic tube and covers the end face of the outer wall of said ceramic tube.

8. The oxygen gas analyzing device as claimed in claim 7 wherein said element extends outwardly beyond the end of said ceramic tube where it is joined with said adhesive.

9. The oxygen gas analyzing device as claimed in claim 8 wherein said adhesive comprises a non-organic adhesive and an organic adhesive, said non-organic adhesive being disposed into said gap between said element and said ceramic tube and said organic adhesive covering said inner wall and said end face of said element, said non-organic adhesive, and said end face and said outer wall of said ceramic tube.

10. The oxygen gas analyzing device as claimed in any of claims 1–9 wherein said partition board extends beyond the surrounding walls of said sampling tube and the extending portion of said partition board is bent in the direction from which gas flows in said flue so that gas flowing in said flue is caught by said bent portion.

11. The oxygen gas analyzing device as claimed in any of claims 1–9 wherein said sampling tube has an outer end formed such that said gas flow-in path is closed in a direction parallel to the direction of flow of said gas in said flue and said gas flow-in path is provided with an opening on the side of said gas sampling tube disposed towards the direction of flow of said gas in said flue.

* * * * *